United States Patent [19]

Daimon et al.

[11] Patent Number: 5,500,404
[45] Date of Patent: Mar. 19, 1996

[54] METHOD FOR DWARFING LILIES AND LILY BULBS OBTAINED FROM THE DWARFING TREATMENT

[75] Inventors: Junko Daimon; Yasuo Takeda, both of Oyama, Japan

[73] Assignee: Japan Tobacco Inc., Tokyo, Japan

[21] Appl. No.: 187,068

[22] Filed: Jan. 27, 1994

[30] Foreign Application Priority Data

Jan. 28, 1993 [JP] Japan ................................. 5-031126

[51] Int. Cl.[6] ..................... A01N 43/653; A01N 43/54; A01N 37/30; A01N 33/12
[52] U.S. Cl. ........................ 504/174; 504/177; 504/181; 504/183
[58] Field of Search ................................. 504/174, 177, 504/181, 183

[56] References Cited

U.S. PATENT DOCUMENTS 4,243,405   1/1981   Balasubramanyan et al. ......... 504/181
4,923,502   5/1990   Elliott et al. ........................... 504/181

FOREIGN PATENT DOCUMENTS 1153024   6/1989   Japan .
4084836   3/1992   Japan .

OTHER PUBLICATIONS

National Research Institute of Vegetables . . . , *Summaries of Experimental Records in Floriculture*, Mar. 1990, Kanto/Tokai, front page and p. 13 (partial translation).

*Primary Examiner*—S. Mark Clardy
*Attorney, Agent, or Firm*—Birch, Stewart, Kolasch & Birch

[57] ABSTRACT

The object of the present invention is to provide a method of lily bulb dwarfing treatment which can be performed before planting, be practiced easily and permit to obtain a uniform dwarfing effect without any special experience and to provide thus dwarfing treated lily bulbs.

Namely, according to the present invention, lily bulbs are submitted to the sprouting treatment, then thus sprouted lily bulbs are soaked in a dwarfing agent.

8 Claims, No Drawings

5,500,404

METHOD FOR DWARFING LILIES AND LILY BULBS OBTAINED FROM THE DWARFING TREATMENT

FIELD OF THE INVENTION

This invention relates to a method for lily bulb dwarfing treatment wherein lily bulbs are submitted to a sprouting treatment and a thus dwarfing treated lily bulb.

BACKGROUND OF THE INVENTION

Lilies are generally tall except for several dwarf species, so that many species are unfit for potting, for instance, in a flower pot, with a conventional cultivation method. In lily cultivation, therefore, the production of lilies suitable for potting is achieved by using drawfing agents.

Paclobutrazol (trade name:Bonzi), Uniconazole (trade name:Sumagic), Ancymidol (trade name:A-Rest), Daminazid (trade name: B-NINE), Chlorocholine chloride (trade name: Cycocel) are used as dwarfing agents for many plants. Conventional dwarfing methods using dwarfing agents consist of spraying the agent on the stem and leaves or pouring the agent into the soil when the plant has grown substantially.

In addition to the dwarfing methods mentioned above, methods consisting of soaking bulbs or seeds in a dwarfing agent or using soil containing a dwarfing agent for cultivation (refer to:TOKKYO-KOKAI-KOHO (18-month Publication of Unexamined Patent Application) HEISEI 1 (1989)-153024 (hereinafter referred to as TOKKAIHEI 1-153024) and other methods are also known.

As for methods for dwarfing a lily, those consisting of conserving lily bulbs for a long period in a refrigerator (refer to: TOKKAIHEI 4-84836) or soaking bulbs in a dwarfing agent before planting are known.

However, problems have been reported for dwarfing methods which include spraying a dwarfing agent on the stem and leaves or pouring it into the soil because the dwarfing treatment can not be performed before planting the lily bulbs, and practioners need some experience and skill given that dwarfing is influenced by the date of treatment or the concentration of dwarfing agent etc.

On the other hand, the method of soaking lily bulbs in a dwarfing agent permits to the dwarfing treatment to be performed before planting, but it has been difficult to obtain uniform dwarfing results because lily sprouts may die, be dwarfed insufficiently or irregularly and similar problems have occurred depending on the dwarfing agent concentration or the treating time. Moreover, other problems such as the occurrence of lower leaves withering or the stem becoming weak have also prevented the method of lily dwarfing by bulb soaking to be practiced.

The present invention has been realized in view of the problems mentioned above and is intended to provide a method of lily bulb dwarfing treatment which can be performed before planting, practiced easily allows for a uniform dwarfing effect to be attained without any special experience and provides dwarfed, treated lily bulbs.

DISCLOSURE OF THE INVENTION

The inventors have eagerly studied methods for lily bulb dwarfing treatment and found, as a result, the object of dwarfing lilies can be achieved by soaking sprouted lily bulbs in a dwarfing agent and thus accomplished the present invention.

More particularly, the first invention concerns a method for lily bulb dwarfing treatment wherein lily bulbs are submitted to a sprouting treatment and then the thus sprouted lily bulbs are soaked in a dwarfing agent.

The second invention concerns a method for lily bulb dwarfing treatment of the first invention above wherein the sprout length of the lily bulb submitted to lily bulb sprouting treatment is 0.5 cm or longer.

The third invention concerns a method for lily bulb dwarfing treatment of the first invention above wherein the sprout length of the lily bulb submitted to lily bulb sprouting treatment is in the range of 0.5 cm to 5.0 cm.

The fourth invention concerns the lily bulbs obtained by the method for dwarfing treatment of the third invention above.

The fifth invention concerns the lily cultivation set comprising a vessel and a lily bulb of the fourth invention above planted in the vessel.

Now, the present invention shall be described in more detail hereunder.

Lily bulbs to be used for the present invention are those conserved and stocked for a short period of less than one (1) year as is a general practice.

Lily bulb sprouting treatment of the present invention shall be performed by gradually heating lily bulbs stocked by freezing or refrigeration (after defrosting), then leaving them at 15° to 25° C. or more preferably about 20° C.

It is preferable that the sprout length of thus treated lily bulbs be 0.5 cm or more and, more preferably, within 0.5 to 5.0 cm. If the sprout is shorter than 0.5 cm, the dwarfing may have no effect on a weak effect and if it is longer than 5.0 cm, sprouts may be damaged during the treatment. Both cases caused undesirable problems.

Dwarfing agents to be used for the present invention are not particularly limited so long as they are used for the dwarfing treatment of plants and to be more specific, Paclobutrazol (trade name: Bonzi), Uniconazole (trade name: Sumagic), Ancymidol (trade name:A-Rest), Daminozide (trade name: B-NINE), Chlorocholine chloride (trade name: Cycocel) and others can be used.

The dwarfing agent concentration to be adopted for the dwarfing treatment of the present invention varies substantially depending on the kind of dwarfing agent to be used, it is generally within the range of 5 ppm to 400 ppm. More particularly, when Paclobutrazol(trade name: Bonzi) is used as dwarfing agent, its preferable concentration is 50 ppm to 400 ppm and its optimal concentration is 100 ppm to 300 ppm. When Uniconazole (trade name:Sumagic) is used, its preferable concentration is 5 ppm to 100 ppm and its optimal concentration is 10 ppm to 50 ppm.

The soaking time in the dwarfing agent to be used for the present invention depends largely on the kind of adopted dwarfing agent and its concentration, however, the preferable soaking time range is 5 to 90 minutes and its optimal time range is 10 to 60 minutes. If the treatment time is shorter than 5 minutes, the dwarfing effect may not become uniform and if it exceeds 90 minutes, lily bulbs may die.

Nevertheless, the present invention is not limited to what is mentioned hereabove, but it is possible to control the lily height by adjusting the concentration of the dwarfing agent to be used for the soaking or by adjusting the soaking time depending on the kind of dwarfing agent or the sprout length.

Using lily bulbs treated in this way, the lily dwarfing can be performed easily and using a cultivation set in which a dwarfing treated lily bulb is planted in a vessel like a flower pot, anyone can cultivate a dwarfed lily easily in a room or elsewhere to be just like ordinary ornamental plants without special care.

As for the vessel used for the lily cultivation set, one can use ordinary plastic pots, porcelain pots, glass pots, planters and others. For the soil, peat moss, Kanuma soil, Akadama soil, Vermiculite or black soil can be used independently or in combination and can be blended with fertilizer or the like beforehand.

According to the present invention, it is possible to obtain dwarfed treated lily bulbs before planting by soaking sprouting treated lily bulbs in a dwarfing agent, and the lily dwarfing can be performed without any treatment after planting.

Additionally, the lily dwarfing method of the present invention allows not only to obtain dwarfed, treated lily bulbs before planting, but also allows the bulbs to be treated according to clear judgement criteria, namely the sprout length, so as to control the dwarfing degree or to regulate the plant height without any special experience.

Moreover, the lily cultivation set can be composed by planting dwarfing treated lily bulbs in a vessel like a flower pot and anyone can enjoy to cultivating a dwarfed lily without special care by using this cultivation set.

DESCRIPTION OF THE PREFERRED EMBODIMENTS

Now, preferred embodiments of the present invention will be described in more detail, however such preferred embodiments are not intended to limit the present invention in any way.

EXAMPLE 1

Casa Blanca (Oriental hybrid) lily bulbs of 19 to 22 cm in circumference were used.

Freeze-stocked lily bulbs were defrosted, heated gradually and left at 20° C. for 10 days to obtain a sprout length of 0.5 to 1.0 cm or left at 20° C. for 14 days to obtain a sprout length of 2.5 to 4.0 cm.

Uniconazole (trade name:Sumagic) was used as the dwarfing agent and the said lily bulbs were soaked in Uniconazole of 25 ppm for 60 minutes.

Each of lily bulbs submitted to the said dwarfing treatment was planted in a No.6 pot with the soil used for the ordinary lily cultivation with non-treated group (without dwarfing treatment) and ten (10) of each group were cultivated in a room.

Each of the lily bulbs whose sprout length is 0 cm (non sprout bulbs) soaked in Uniconazole of 25 ppm for 60 minutes (treated group) and non sprout bulbs without soaking (non treated group) were also planted in a No.6 pot and ten (10) of each group were cultivated in a room.

Lily bulbs were planted on January the 31st and cultivated with ordinary care.

No difference in days required for flowering was observed between the groups and no withered lower leaves nor weak stem was observed in either the treated group or the non-treated group.

On the 123rd day (June the 2nd), the number of flowers per plant and the height from the ground to the flower top were measured to obtain the average.

The result is shown in Table 1.

TABLE 1

| Sprout length (cm) | Group | Plant height (cm) | Number of flowers per pot |
|---|---|---|---|
| 0 | Non-treated | 115 | 4.7 |
|  | Treated | 112 | 4.6 |
| 0.5 to 1.0 | Non-treated | 112 | 4.5 |
|  | Treated | 25 | 4.2 |
| 2.5 to 4.0 | Non-treated | 113 | 4.0 |
|  | Treated | 17 | 3.8 |

As obviously sown in Table 1, no dwarfing effect was observed in the group where non sprouted bulbs were soaked in a dwarfing agent while the effect was recognized in the group where sprouted bulbs were soaked. Moreover, we found that the longer the sprout was when bulbs were soaked, the higher was the dwarfing effect.

EXAMPLE 2

Casa Blanca (Oriental hybrid) lily bulbs of 19 to 22 cm in circumference were used as in the Example 1.

Freeze-stocked lily bulbs were defrosted, heated gradually and left at 20° C. for 10 days to obtain a sprout length of 0.5 to 1.0 cm or left at 20° C. for 14 days to obtain a sprout length of 2.5 to 4.0 cm.

Paclobutrazol (trade name:Bonzi) was used as the dwarfing agent and the said lily bulbs were soaked in Paclobutrazol of 200 ppm for 20 minutes.

Each of lily bulbs submitted to the said dwarfing treatment was planted in a No. 6 pot with the soil used for the ordinary lily cultivation with non-treated group (without dwarfing treatment) and ten (10) of each group were cultivated in a room.

Each of the lily bulbs whose sprout length was 0 cm (non sprout bulbs) soaked in Paclobutrazol of 200 ppm for 20 minutes (treated group) and non sprout bulbs without soaking (non treated group) were also planted in a No. 6 pot and ten (10) of each group were cultivated in a room.

Lily bulbs were planted on January the 31st and cultivated with ordinary care.

No difference in days required for flowering was observed between the groups and no withered lower leaves nor weak stem was observed in either the treated group or the non-treated group.

On the 123rd day (June the 2nd), the number of flower per plant and the height from the ground to the flower top were measured to determine the average.

The result is shown in Table 2.

TABLE 2

| Sprout length (cm) | Group | Plant height (cm) | Number of flowers per pot |
|---|---|---|---|
| 0 | Non-treated | 115 | 4.7 |
|  | Treated | 117 | 4.1 |
| 0.5 to 1.0 | Non-treated | 112 | 4.5 |
|  | Treated | 45 | 4.3 |
| 2.5 to 4.0 | Non-treated | 113 | 4.0 |
|  | Treated | 20 | 3.8 |

As obviously shown in Table 2, no dwarfing effect was observed in the group where non sprouted bulbs were soaked in a dwarfing agent while the effect was recognized in the group where sprouted bulbs were soaked. Moreover, we had found that the longer the sprout was when bulbs were soaked, the higher was the dwarfing effect.

EXAMPLE 3

Casa Blanca (Oriental hybrid) lily bulbs of 19 to 22 cm in circumference were used as in the Example 1.

Freeze-stocked lily bulbs were defrosted, heated gradually and left at 20° C. for 10 days to obtain a sprout length of 0.5 to 2.0 cm.

Uniconazole (trade name:Sumagic) and Paclobutrazol (trade name: Bonzi) were used as dwarfing agent and the said lily bulbs were soaked changing the treatment parameters such as the concentration of the dwarfing agents and the soaking time as shown in the Table 3.

Each of lily bulbs submitted to the said dwarfing treatment was planted in a No. 6 pot with the soil used for the ordinary lily cultivation with non-treated group (without dwarfing treatment) and ten (10) of each group were cultivated in a greenhouse.

Lily bulbs were planted on April the 9th and cultivated with ordinary care.

No difference in days required for flowering was observed between the groups and no withered lower leaves nor weak stem was observed in either the treated group or the non-treated group.

On the 97th day (July the 15th), the number of flower per plant and the height from the ground to the flower top were measured to determine the average.

The result is shown in Table 3.

TABLE 3

| Dwarfing agent | Concentration (ppm) | Soaking time (min.) | Plant height (cm) | Number of flowers per pot |
| --- | --- | --- | --- | --- |
| Uniconazole | 25 | 30 | 18 | 3.6 |
| | 25 | 60 | 16 | 3.4 |
| | 50 | 30 | 15 | 4.0 |
| | 50 | 60 | 10 | 5.8 |
| Paclobutrazol | 100 | 10 | 42 | 4.6 |
| | 100 | 20 | 40 | 4.8 |
| | 100 | 30 | 36 | 3.4 |
| | 100 | 60 | 32 | 3.2 |
| | 200 | 10 | 34 | 5.3 |
| | 200 | 20 | 32 | 5.2 |
| | 200 | 30 | 27 | 3.2 |
| | 200 | 60 | 25 | 3.3 |

As shown in Table 3, it was found that Uniconazole was more effective than Paclobutrazol at a lower concentration and for the same dwarfing agent, it was more effective at higher concentration and longer treatment time.

EXAMPLE 4

Casa Blanca (Oriental hybrid) lily bulbs of 19 to 22 cm in circumference were used as in the Example 1.

Freeze-stocked lily bulbs were defrosted, heated gradually and left at 20° C. for 10 days to obtain a sprout length of 0.5 to 2.0 cm.

Paclobutrazol (trade name: Bonzi) was used as the dwarfing agent and the said lily bulbs were soaked in Paclobutrazol of 100 ppm for 30 minutes.

The said dwarfing treatment was performed immediately before the planting and then bulbs were planted on different date, as in the Example 1, in a No. 6 pot with the soil used for the ordinary lily cultivation with non-treated group (without dwarfing treatment) and ten (10) of each group were cultivated in a greenhouse.

Lily bulbs were planted on April the 21st and June the 24th and cultivated with ordinary care.

No difference in days required for flowering was observed between the treated group and the non-treated group, however the difference was noted according to the planting date. After the flowering, namely on the 90th day (July the 20th) and on the 65th day (August the 28th), the number of flower per plant and the height from the ground to the flower top were measured to determine the average.

The result is shown in Table 4.

TABLE 4

| Planted date | Group | Plant height (cm) | Number of days requiered for flowering | No. of flowers per pot |
| --- | --- | --- | --- | --- |
| Apr. 21 | Non-treated | 90 | 90 | 2.7 |
| | Treated | 60 | 90 | 3.7 |
| Jun. 24 | Non-treated | 81 | 65 | 3.6 |
| | Treated | 41 | 65 | 3.4 |

It was made obvious from Table 4 that, with the same treatment parameters, the height of lily and the number of days required for flowering varied according to the planted date and more evident dwarfing effect could be achieved by planting them in June than in April.

EXAMPLE 5

Le Rĕve (Oriental hybrid) lily bulbs of 13 to 15 cm in circumference were used.

Freeze-stocked lily bulbs were defrosted, heated gradually and left at 20° C. for 14 days to obtain a sprout length of 2.5 to 4.0 cm.

Uniconazole (trade name:Sumagic) and Paclobutrazol (trade name: Bonzi) were used as dwarfing agent and the said lily bulbs were soaked changing the treatment parameters such as the concentration of the dwarfing agents and the soaking time as shown in Table 5.

Each of lily bulbs submitted to the said dwarfing treatment was planted in a No. 6 pot with the soil used for the ordinary lily cultivation and ten (10) of each group were cultivated in a greenhouse.

Lily bulbs were planted on September the 13th and cultivated with ordinary care.

No difference in days required for flowering was observed between the groups and no withered lower leaves nor weak stem was observed in either the treated group or the non-treated group.

On the 67th day (November the 19th), the number of flower per plant and the height from the ground to the flower top were measured to determine the average.

The result is shown in Table 5.

TABLE 5

| Dwarfing agent | Concentration (ppm) | Soaking time (min.) | Plant height (cm) | Number of flowers per pot |
| --- | --- | --- | --- | --- |
| Non-treated | — | — | 28 | 2.5 |
| Uniconazole | 25 | 60 | 7 | 2.4 |
| | 50 | 60 | 5 | 2.0 |
| Paclobutrazol | 200 | 60 | 20 | 1.5 |
| | 300 | 60 | 9 | 1.7 |

From Table 5, it was found that the dwarfing effect by a dwarfing agent could be obtained also with Le Rĕve, species other than Casa Blanca.

We claim:

1. A method for lily bulb dwarfing treatment which comprises subjecting a lily bulb to conditions which cause sprouting, and then soaking the sprouted lily bulb in a dwarfing agent, wherein the sprout of said sprouted lily bulb has a length in the range of 0.5 cm to 5.0 cm.

2. The method for lily bulb dwarfing treatment of claim 1, wherein said conditions include exposure of said lily bulb to a temperature of 15° to 25° C.

3. The method for lily bulb dwarfing treatment of claim 1, wherein said dwarfing agent is paclobutrazol.

4. The method for lily bulb dwarfing treatment of claim 1, wherein said sprouted lily bulb is soaked for 5 to 90 minutes in a dwarfing agent.

5. The method for lily bulb dwarfing treatment of claim 1, wherein said sprouted lily bulb is soaked for 10 to 60 minutes in a dwarfing agent.

6. The method for lily bulb dwarfing treatment of claim 1, wherein said conditions include exposure of said lily bulb to a temperature of 15° to 20° C.

7. The method for lily bulb dwarfing treatment of claim 6, wherein said dwarfing agent is paclobutrazol.

8. The method for lily bulb dwarfing treatment of claim 7, wherein said sprouted lily bulb is soaked for 10 to 60 minutes in a dwarfing agent.

* * * * *